United States Patent [19]

McCurry, Jr. et al.

[11] Patent Number: 5,519,124
[45] Date of Patent: May 21, 1996

[54] PRODUCTION OF ALKYLPOLYGLYCOSIDES

[75] Inventors: Patrick M. McCurry, Jr., Lansdale, Pa.; Carl E. Pickens, Fairfield, Ohio

[73] Assignee: Henkel Corporation, Plymouth Meeting, Pa.

[21] Appl. No.: 152,111

[22] Filed: Nov. 12, 1993

[51] Int. Cl.$^6$ .............. C07H 1/06; C07H 15/04; C07G 3/00
[52] U.S. Cl. .............. 536/18.5; 536/18.6; 536/127
[58] Field of Search .............. 536/127, 18.5, 536/18.6

[56] References Cited

U.S. PATENT DOCUMENTS

| | | | |
|---|---|---|---|
| 4,393,203 | 7/1983 | Mao et al. | 536/124 |
| 4,987,225 | 1/1991 | Pickens et al. | 536/124 |
| 5,079,350 | 1/1992 | Fujita et al. | 536/18.6 |

FOREIGN PATENT DOCUMENTS 418458  3/1991  European Pat. Off. .

*Primary Examiner*—Douglas W. Robinson
*Assistant Examiner*—Everett White
*Attorney, Agent, or Firm*—Ernest G. Szoke; Wayne C. Jaeschke; Patrick J. Span

[57] ABSTRACT

An improvement in the process of preparation of an alkylpolyglycoside containing a long chain alkyl group of about 10 carbon atoms or more by reaction of a saccharide and a long chain alcohol in the presence of an acid catalyst, particularly an improvement in the process to inhibit or minimize condenser fouling during the processing either in the removal of water from the reactor to promote completion of the reaction or in subsequent processing of the reaction product stream wherein the stream is heated at elevated temperatures and vacuum to remove excess alcohol and residual water, or water introduced into the process stream by steam ejectors in an evaporator, after leaving the reactor. The improvement includes the addition of an alcohol having a carbon chain of a number less than the carbon chain of the alkyl group of the alkylpolyglycoside product either along with the reactant alcohol to produce the polyglycoside, or to the product stream at evaporation of the excess alcohol and residual water.

13 Claims, 1 Drawing Sheet

PRODUCTION OF ALKYLPOLYGLYCOSIDES

BACKGROUND OF THE INVENTION

1. Field of the Invention

This invention relates to the preparation of alkylpolyglycosides by the reaction of a saccharide and an alcohol in the presence of an acid catalyst, and particularly to an improvement in the process to inhibit condenser fouling during the processing either in the removal of water from the reactor to promote completion of the reaction or in subsequent processing of the alkylpolyglycoside reaction product stream wherein the stream is heated at elevated temperatures and vacuum, i.e. evaporation or distillation to remove excess alcohol and any residual water remaining in the stream after leaving the reactor (e.g. via steam ejectors).

2. Statement of Related Art

Alkyl glycosides are conveniently prepared by reacting an alcohol of the type and chain length which is desired to form the "alkyl" portion of the glycoside of interest with a saccharide reactant (e.g., a monosaccharide such as glucose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl glycoside product of interest. Typically, such reaction is conducted at an elevated temperature and in the presence of an acid catalyst. Various alkyl glycoside products and processes for making same are disclosed in a variety of representative patents.

U.S. Pat. No. 4,987,225 contains an extensive listing of processes for preparing alkylpolyglycosides, the description of which is hereby incorporated by reference. Included therein is U.S. Pat. No. 4,393,203 to Mao et al (issued Jul. 12, 1983) which includes the step of removal of the excess alcohol in a thin film evaporator. U.S. Pat. No. 5,079,350 further describes a method for removing unreacted alcohol from the glycoside surfactant product by contacting the alkylpolyglycoside and alcohol mixture with a spraying stream of inert gas under reduced pressure in a thin film evaporator maintained at a temperature in the range of about 140° C. to about 200° C. The process is described as substantially removing all of the unreacted alcohol and odor from the glycoside product.

In the process, condensers are employed at the reactor stage and at the removal of excess alcohol stage. In the condenser a gel-like emulsion frequently forms presenting condenser plugging problems, the severity of which varies with the alcohol source, particularly those containing a long carbon chain, i.e., 10 or more carbons. It was demonstrated in the laboratory that the gel-like emulsion which typically forms is an emulsion of only the alcohol components and water, in which a film of alcohol surrounds droplets of water. The gel formed in the laboratory only contains alcohol and water. In commercial larger scale operations, the possibility exists that during upset conditions, for example entrainment, a more complex gel structure may be present which may include some alkylpolyglycoside itself and the saccharide i.e. glucose.

BRIEF DESCRIPTION OF THE DRAWING

The FIGURE is a laboratory scale configuration used to illustrate and exemplify the invention.

BRIEF SUMMARY OF THE INVENTION

Figure 1:
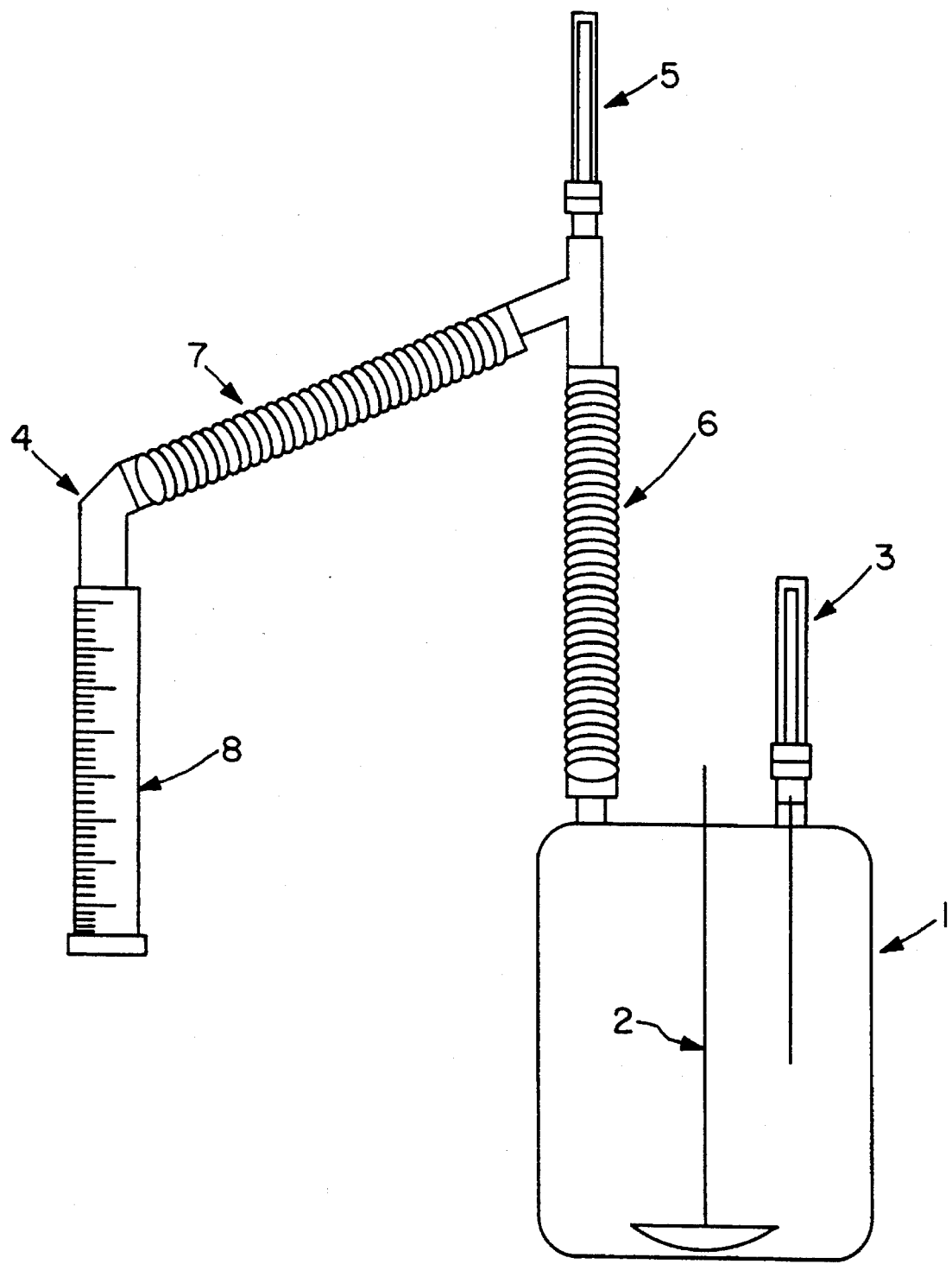

It has now been discovered that condenser fouling can be eliminated or inhibited in a process of preparing alkylpolyglycosides in which the alkyl group is a long chain alkyl group containing 10 or more carbon atoms, such as about 10 to about 20 carbon atoms, by addition to the long chain alkylpolyglycoside stream containing the 10–20 carbon alkyl group polyglycoside, alcohol and water, of another second, alcohol containing a lesser number of carbon atoms, i.e., less than 10, preferably about 4–8 carbon atoms, than the alkyl group in the long chain carbon atom alkylpolyglycoside stream.

DESCRIPTION OF THE INVENTION

Other than in the operating examples, or where otherwise indicated, all numbers expressing quantities, or reaction conditions used herein are to be understood as modified in all instances by the term "about".

In view of the summary above, it is accordingly an object of the invention to provide an improved process for preparing alkylpolyglycosides having a long chain alkyl group of 10 or more carbon atoms, of a saccharide reacted with an alcohol having 10 or more carbon atoms, in the presence of an acid catalyst at elevated temperatures, after which the acid catalyst is neutralized and the excess alcohol removed. The improvement in the process is the elimination or inhibition of condenser fouling during the reaction and in the removal of excess alcohol and water from the alkylpolyglycoside reaction product stream, by the addition of an alcohol containing a number of carbon atoms less than the number of carbon atoms in the alkyl group of the alkylpolyglycoside reaction product from the long chain alcohol.

The second alcohol added to eliminate or minimize the condenser fouling resulting from the long chain alcohol and water, may be a primary or secondary alcohol and will contain components with less than the 10 carbon atoms of the long chain alcohol length. The preferred shorter chain second alcohol, preferably will contain components with about 4 to about 9 carbon atoms. This second alcohol may also be defined by the formula R—CH$_2$—OH or

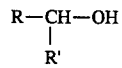

where R and R' are aliphatic or aromatic hydrocarbon groups with a total of from 1 to about 9 carbon atoms, and preferably at least 3 carbon atoms.

As described in the related art section above, the initial reaction product of the alcohol and saccharide in the presence of an acid catalyst results in a glycoside product. The product is a mixture of a monoglycoside of the alcohol and various higher degrees of polymerization (DP) polyglycosides in progressively decreasing mole percentage amounts, i.e., the diglycoside (DP2), the triglycoside (DP3) and the higher polyglycosides (DP4 and higher). The typical, statistical distribution of the various oligomers provided referred to as a Flory distribution. While the specific distribution of the various fractions may vary somewhat for various reaction products, the overall distribution curve is the same, though the average DP of the reaction mixture may vary due to the differing distribution of the various fractions, i.e., DP1, DP2, DP3 and higher fractions. Typically, the Flory distribution of the reaction product after removal of the excess alcohol will have an average degree of polymerization above 1.2, i.e., about 1.4, with a monoglycoside content in the range of about 50–70% by weight of the glycoside product. Commercially available products typically have an average Flory DP of about 1.3–1.7.

The glycoside products of the reaction of an alcohol and saccharide may be represented by the formula I:

$$ROG_x \qquad (I)$$

wherein R is a residue of an alcohol, o is oxygen, G is a glycoside residue, and x is the average degree of polymerization (DP) resulting from weighting of the various mono-, di-, tri- and higher glycoside fractions present in the product and is a number of from about one to about three.

The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycoside having corresponding more rings, the average of which in the currently available commercial product therefore being typically greater than about 1, generally in the order of about 1.2 to about 1.7, with preferred mixtures at about 1.3 to about 1.7.

The alkylpolyglycoside products represented by the formula above contain a lipophilic group, the R group, and a hydrophilic group, the $OG_x$ group. For detergent or surfactant-use application, the product should have a hydrophilic-lipophilic balance (HLB) of from about 10 to about 16, and preferably about 11 to about 14. The HLB value of a product may be calculated by the formula $$HLB = \frac{([MW_{AGU}] \times DP + MW_O)}{(([MW_{AGU}] \times DP + MW_O) + MW_R)} \times 100/5$$

where AGU is typically the anhydro glucose unit in G having a molecular weight of 162, $MW_O$ is the molecular weight of oxygen and $MW_R$ is the molecular weight of the R group, and DP is the average degree of polymerization as predicted by Flory's statistical treatment.

The lipophilic R groups in the alkylpolyglycosides are derived from alcohols, preferably monohydric, for the detergent, surfactant-use applications and should contain from about 10 to about 20, preferably about 10 to about 18 carbon atoms, with an average of about 10 to about 14 being most preferred, to provide R groups of sufficient length for detergent, surfactant-use applications. While the preferred R groups are saturated aliphatic or alkyl, there may be present some unsaturated aliphatic hydrocarbon groups. Thus, the preferred groups are derived from the fatty alcohols derived from the naturally-occurring fats and oils, such as octyl, decyl, dodecyl, tetradecyl, hexadecyl, octadecyl, oleyl and linoleyl, but R groups may be derived from synthetically produced Ziegler alcohols or oxo alcohols containing 9, 10, 11, 12, 13, 14 or 15 carbon atoms. The alcohols of naturally-occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process contain both an odd and even number of carbon atoms such as the $C_9$–$C_{15}$ mixtures, which are also available commercially.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g. methyl glycoside, ethyl glycoside, propyl glycoside, butyl glycoside, etc.), oligosaccharides (e.g. sucrose, maltose, maltotriose, lactose, xylobiose, melibiose, cellobiose, raffinose, stachyose, etc.) and other polysaccharides. Such saccharide reactants may be employed in dry (e.g. anhydrous) form or, if desired, may be employed in the form of hydrated solids or aqueous solutions thereof. If utilized in the form of a solution, it is preferred that the resulting reaction mixture contain only small amounts of water, i.e., less than about 1% by weight, preferably less than about 0.5% i.e. less than 0.25% or 0.1%.

While the details of the preparation of the initial alkyl glycosides reaction mixture employed in the present invention only indirectly form a part of the present invention, a brief description generally of the preparation follows. The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. Preferably, the ratio of alcohol to monosaccharide will be chosen to allow the production of an alkyl glycoside product having a DP between about 1.2 to about 1.7, and more preferably about 1.3 and about 1.6.

The reaction between the hydrophobic alcohol reactant and the saccharide reactant to form the glycoside surfactant is typically conducted at an elevated temperature and in the presence of an acid catalyst. As a general rule, said reaction is preferably conducted at a temperature of from about 80° to about 140° C., preferably about 90° to about 120° C., and at pressures (about 10 to about 100 mm Hg absolute), which facilitate water removal, while at the same time maintaining the desired reaction temperatures.

Acid catalysts suitable for use include strong mineral acids such as hydrochloric acid, sulfuric acid, nitric acid, phosphoric acid, hypophosphorous acid, etc.; strong organic acids such as para toluenesulfonic acid, methanesulfonic acid, trifluoromethanesulfonic acid, mono- or polyalkylated aryl mono- or polysulfonic acids such as dodecylbenzenesulfonic acid, alpha-sulfocarboxylic acids or esters, etc.; and macroreticular acidic ion exchange resins such as macroreticular sulfonic acid ion exchange resins, perfluorinated sulfonic acid resins, etc. Typically, said acid catalyst will be employed in an amount ranging from about 0.0005 to about 0.03 (preferably from about 0.002 to about 0.015) moles thereof per mole of saccharide used.

Typically, the above-described reaction process will be conducted over a reaction period of from about 1 to about 20 (preferably from about 2 to about 10) hours. Upon completion of the reaction, the acid catalyst is typically neutralized by an alkaline substance, preferably an alkali metal hydroxide such as sodium hydroxide, used in an amount about equal, on a stoichiometric basis, to the amount of material needed to neutralize the catalyst. For the present invention, most preferably the mixture is neutralized and adjusted to a pH in the range of about 9 to about 12 with an alkali metal hydroxide and alkaline earth metal oxide, such as magnesium oxide, prior to removal of the alcohol.

After neutralization of the acid catalyst, typically excess unreacted alcohol is removed. Alcohol removal is generally accomplished by evaporation, e.g. distillation, of the alcohol. The use of a wiped film or thin film evaporator is particularly convenient for this purpose, preferably operated at about 150°–220° C. and about 0.1 to about 50 mm Hg pressure. More generally pressures of about 1 to about 100 mm Hg and temperatures of about 140° to about 230° C. may be employed.

At this point, the resulting commercial product, substantially devoid of alcohol, is typically a mixture of alkyl glycosides, in which for purposes of this invention the alkyl group will contain from about 10 to about 20, preferably about 10 to about 18, most preferably an average of about 10 to about 14, carbon atoms, having the typical Flory distribution discussed earlier above.

After removal of the excess alcohol to a level less than about 5% and preferably less than about 1% by weight, the substantially alcohol-free product is then typically bleached, prior to recovery.

As indicated earlier, in preparing alkylpolyglycosides in which the alkyl group contains 10 or more carbon atoms from the reactant alcohol, condenser fouling occurs. On a laboratory scale as shown in FIG. 1 the gel-like emulsion which causes condenser fouling is found to be an emulsion of alcohol and water, apparently a water/oil/water (W/O/W) emulsion, which under microscopic examination appears to consist of small spheres suspended in a continuous phase. From about 2 to 20 minutes after vacuum is broken, the gel breaks down and the small spheres burst releasing their contents. Gel formation was studied in laboratory equipment shown in FIG. 1 in which the vessel or reactor is represented by the numeral 1, containing a stirrer 2. Water may be added below the liquid surface of the reactor through funnel 3. In this study, vacuum is applied through port 4, at temperatures between 76° and 110° C.

Solvent addition, alcohol, is accomplished through funnel 5. A partial condenser 6 extends from the reactor vessel 1 and a final condenser 7 deposits the distillate into receiver 8.

To simulate the gel which is formed during commercial production of an alkylpolyglycoside in which the alkyl group contains 10 or more carbon atoms, water is added to a flask 1 containing an alcohol at typical reaction conditions. The rate of water addition was equal to the rate of water evolution experienced during the reactions in producing alkylpolyglycoside.

All batches were produced in a 5 liter flask using Alfol $C_{10}$ alcohol (contains approximately 0.3% $C_8$ alcohol). In all cases water was introduced below the alcohol level in the flask. The flask did not contain dextrose or polyglycoside during these experiments. The vapor from the reactor flask passes through the coils of the partial condenser 6, then the vapor passes through the shell side of the final condenser 7. Gel typically forms on the coils in the final condenser.

Generally, gel formed by addition of water below the surface of the reactor under vacuum at temperatures between 76° and 110° C. The rate of gel formation appeared to be directly related to the rate of water addition, but the temperature of the liquid (between 76° and 110° C.) did not appear to be strongly related to the rate of gel formation. The milky white gel is very tenacious, but it can be removed from the condenser and subjected to microscopic examination, with the observations noted earlier above. The following Table I shows the relative proportion of water and alcohol in a typical gel sample.

TABLE I

|  | Volume % | Mass % | Mol % |
|---|---|---|---|
| Alcohol | 9.5 | 7.9 | 1 |
| Water | 90.5 | 92.1 | 99 |

In one phase of the experiment, temperature variation was studied to determine whether gel formation could be eliminated by changing the temperature of the partial or final condensers. In this phase, the temperature of the partial condenser 6 was adjusted between 30° and 45° C. The temperature of the final condenser was adjusted between 9° and 35° C. Gel formed in the condenser under all conditions tested.

In another phase, the condenser temperatures were set to their typical laboratory values (partial condenser: 45° C.; final condenser: 9° C. A small quantity of butanol (2 ml) was added to the system above the partial condenser. The gel which previously formed in the final condenser immediately began to break down.

An attempt was made to break down the gel using $C_8$ alcohol. Large amounts (up to 200 ml) above the partial condenser did not break down gel but did inhibit the formation of the gel during the experiment.

Five weight % of the octanol was added to the $C_{10}$ alcohol in the flask before the addition of water. Water was then added to the flask in the manner earlier described. Gel did not form in either of the condensers.

The composition of one gel alcohol phase in the course of the investigation, produced using only Alfol $C_{10}$ alcohol, can be seen from the following Table II.

TABLE II

| Alcohol | Weight % |
|---|---|
| $C_6$ | 0.17 |
| $C_8$ | 2.01 |
| $C_9$ | 0.30 |
| $C_{10}$ | 97.00 |
| $C_{11}$ | 0.35 |
| $C_{12}$ | 0.17 |

While periodic replacement of the condenser cooling water with steam might be employed to break down the gel, this is disadvantageous and inconvenient in operation of a continuous, commercial production which would result in temporary loss of vacuum, increased shut-down time, and the expense of additional wear and tear on equipment. In fact, during runs with alcohols of chain length greater than $C_{10}$, using steam on the process side (e.g. steam ejectors in an evaporator) can result in severe fouling of the vacuum system intercondensers. Injection of from about 0.01 to 0.1% by weight of a 55:45 mixture of $C_8$–$C_{10}$ alcohol (based on the weight of the evaporator feed) just upstream of the stream jet eliminates fouling of the intercondensers.

We claim:

1. A method of eliminating or inhibiting condenser fouling in a process of preparation of an alkylpolyglycoside in which the alkyl group contains 10 or more carbon atoms, which process comprises reacting in a reactor a saccharide and a long chain alcohol or mixture of alcohols in the presence of an acid catalyst and removing water and alcohol from the reaction product stream containing excess alcohol and water, said method comprising (a) providing an alkylpolyglycoside reaction product stream containing a long chain alcohol or mixture of alcohols having 10 or more carbon atoms and water;

(b) adding to said alkylpolyglycoside reaction product stream a second alcohol or mixture of alcohols containing a lesser number of carbon atoms then the alkyl group in the alkylpolyglycoside stream; and (c) removing the water and alcohol by heating said stream under vacuum to vaporize the water and alcohol and condensing on condenser surfaces the water and alcohol;

whereby the formation of a gel phase of the long chain alcohol and water on the condenser surfaces is inhibited or eliminated.

2. A method as defined in claim 1 in which the alkylpolyglycoside stream is the reaction product of the saccharide and an alcohol having from 10 to about 20 carbon atoms and the water is water of hydration and water of reaction which is removed from the reactor during the reaction to permit the reversible glycoside reaction to proceed to completion.

3. A method as defined in claim 2 wherein the alcohol providing the alkyl group of the alkylpolyglycoside contains from about 10 to about 18 carbon atoms.

4. A method as defined in claim 1 wherein said second alcohol contains less than 10 carbon atoms.

5. A method as defined in claim 4 wherein the second alcohol contains from about 4 to about 8 carbon atoms.

6. A process as defined in claim 1, wherein water being removed includes water introduced into the process stream by steam ejectors in an evaporator.

7. A process as defined in claim 1 wherein the alkylpolyglycoside stream is the reaction product stream leaving the reactor and introduced to an evaporator to remove the excess alcohol and residual water remaining in the stream after removal of the water of reaction.

8. A method as defined in claim 7, wherein the excess alcohol is evaporated at a temperature from about 140° C. to about 230° C. and a pressure less than about 100 mm Hg.

9. A method as defined in claim 8 wherein the temperature is about 150° C. to about 220° C. and a pressure of about 1 to about 100 mm Hg.

10. A process as defined in claim 1 wherein the second alcohol has the formula R—CH$_2$—OH or $$R\text{---}\underset{\underset{R'}{|}}{CH}\text{---}OH$$

where R and R' are aliphatic or aromatic hydrocarbon groups having a total of from 1 to about 9 carbon atoms.

11. A method as defined in claim 1 wherein the water is removed during the reaction at a pressure of about 10 to about 100 mm Hg.

12. A method as defined in claim 1 wherein the second alcohol is added to the reactor along with the alcohol being reacted with the saccharide.

13. In a process of preparing an alkylpolyglycoside in which the alkyl group contains at least 10 carbon atoms comprising reacting a saccharide and a primary alcohol in the presence of an acid catalyst to provide a reaction product stream containing the alkylpolyglycoside, water of reaction and excess alcohol and removing the excess alcohol from the reaction product stream, the improvement comprising adding to said reaction product stream a second alcohol having from about 4 to about 9 carbon atoms, after which the stream is heated under vacuum at an elevated temperature to vaporize the alcohol and water in the stream and the water and alcohol is condensed on condenser surfaces, whereby a gel phase of water and alcohol on the condenser surfaces is eliminated or minimized.

* * * * *